US012251725B2

(12) United States Patent
Glasbey et al.

(10) Patent No.: US 12,251,725 B2
(45) Date of Patent: Mar. 18, 2025

(54) MEDICAL LUBRICANT APPLICATOR (71) Applicant: Whiteley Corporation Pty Ltd, North Sydney (AU)

(72) Inventors: Trevor Glasbey, Tanilba Bay (AU); Gregory Whiteley, Queenscliff (AU)

(73) Assignee: Whiteley Corporation Pty Ltd, North Sydney (AU)

( * ) Notice: Subject to any disclaimer, the term of this patent is extended or adjusted under 35 U.S.C. 154(b) by 204 days.

(21) Appl. No.: 17/641,492

(22) PCT Filed: Aug. 21, 2020

(86) PCT No.: PCT/AU2020/050872
§ 371 (c)(1),
(2) Date: Mar. 9, 2022

(87) PCT Pub. No.: WO2021/046591
PCT Pub. Date: Mar. 18, 2021

(65) Prior Publication Data
US 2022/0305520 A1  Sep. 29, 2022

(30) Foreign Application Priority Data
Sep. 11, 2019  (AU) ............................ 2019903370

(51) Int. Cl.
*A61B 1/00* (2006.01)
*A61J 1/00* (2023.01)
(Continued)

(52) U.S. Cl.
CPC .... *B05C 17/00516* (2013.01); *A61B 1/00131* (2013.01); *A61J 1/00* (2013.01);
(Continued)

(58) Field of Classification Search
CPC .......... A61B 1/00131; B05C 17/00516; B05C 17/00583; B05C 17/00503; B05C 17/10; B65D 55/16; A61J 1/00
See application file for complete search history.

(56) References Cited

U.S. PATENT DOCUMENTS 3,193,146 A * 7/1965 Isgriggs .............. B05C 17/0123
222/326
6,755,586 B1   6/2004 Frazier
(Continued)

FOREIGN PATENT DOCUMENTS

CN        208808445 U    5/2019

OTHER PUBLICATIONS

International Search Report in PCT/AU2020/050872 (Oct. 23, 2020).
(Continued)

*Primary Examiner* — Frederick C Nicolas
(74) *Attorney, Agent, or Firm* — Pryor Cashman LLP (57) ABSTRACT

A medical lubricant applicator including: a dispensing head adapted to fit to a container containing a medical lubricant, the dispensing head including: (i) a nozzle having a discharge opening from which medical lubricant from the container is dispensed; (ii) a guide element arranged relative to the nozzle to provide guiding contact with an exposed surface of a medical instrument to which the dispensed medical lubricant is to be applied whereby in operation the nozzle is with the assistance of the guide element spaced from the exposed surface of the medical instrument to avoid contact with the exposed surface whilst the medical lubricant is directed toward the exposed surface for application of the lubricant to the exposed surface via the discharge opening of the nozzle.

12 Claims, 5 Drawing Sheets

(51) Int. Cl.
  *B05B 11/04* (2006.01)
  *B05C 17/005* (2006.01)
  *B65D 55/16* (2006.01)
  *B05C 17/10* (2006.01)
(52) U.S. Cl.
  CPC ........ *B05C 17/00583* (2013.01); *B65D 55/16* (2013.01); *B05C 17/10* (2013.01)

(56) References Cited

U.S. PATENT DOCUMENTS

| | | | |
|---|---|---|---|
| 7,614,811 B2 * | 11/2009 | Kaufman | A61M 35/006 401/133 |
| 11,377,263 B2 * | 7/2022 | Gydesen | A61J 1/1412 |
| 2004/0226968 A1 * | 11/2004 | Lafond | B05C 17/00513 222/327 |
| 2009/0112064 A1 * | 4/2009 | Levey | A61B 1/12 600/114 |
| 2011/0137121 A1 | 6/2011 | Itoi | |
| 2017/0319838 A1 | 11/2017 | Kaufman et al. | |
| 2018/0345302 A1 * | 12/2018 | Tayh | B65D 47/2031 |
| 2022/0079425 A1 * | 3/2022 | Miller | A61B 1/00131 |

OTHER PUBLICATIONS

Written Opinion of the International Searching Authority in PCT/AU2020/050872 (Oct. 23, 2020).

\* cited by examiner

MEDICAL LUBRICANT APPLICATOR

TECHNICAL FIELD

The present invention relates broadly to a medical lubricant applicator and is directed more particularly, although not exclusively, to a dispensing head of a medical lubricant applicator for applying medical lubricant to a medical instrument.

BACKGROUND OF INVENTION

For medical staff it is common practice to lubricate the sheath of an endoscope or colonoscope prior to its insertion. The sheath is lubricated with a gel discharged into a gloved hand which is run along a section of the sheath to be lubricated. In a clinical environment where infection prevention is critically important, this practice is not ideal having an unacceptable risk of cross-contamination resulting in patient infection.

SUMMARY OF INVENTION

According to a first aspect of the present invention there is provided a medical lubricant applicator comprising:
a dispensing head adapted to fit to a container containing a medical lubricant, the dispensing head including:
i) a nozzle having a discharge opening from which medical lubricant from the container is dispensed;
ii) a guide element arranged relative to the nozzle to provide guiding contact with an exposed surface of a medical instrument to which the dispensed medical lubricant is to be applied whereby in operation the nozzle is with the assistance of the guide element spaced from the exposed surface of the medical instrument to avoid contact with said exposed surface whilst the medical lubricant is directed toward the exposed surface for application of said lubricant to said exposed surface via the discharge opening of the nozzle.

Preferably the guide element includes a contact member mounted to a spacer member arranged to space the nozzle from the exposed surface of the medical instrument. More preferably the contact member is in profile shaped arcuate to assist with lateral location of the medical instrument relative to the nozzle to promote application of the medical lubricant to the exposed surface of the medical instrument. Even more preferably the contact member is at least in part formed of a resiliently flexible material adapted to facilitate sliding contact of the contact member with the exposed surface of the medical instrument whilst reducing the likelihood of damage to said exposed surface.

Additionally or alternatively the guide element includes another contact member mounted to the spacer member to laterally locate the exposed surface of the medical instrument relative to the nozzle to promote application of the medical lubricant to said exposed surface. In this embodiment the other contact member may in profile be shaped arcuate to assist with spacing of the exposed surface of the medical instrument from the nozzle. In this case the other contact member is at least in part formed of a resiliently flexible material adapted to facilitate sliding contact of the contact member with the exposed surface of the medical instrument nozzle. In a variation on this embodiment the other contact member and the contact member are formed continuous with one another.

Preferably the dispensing head also includes a coupling arrangement for detachable fitting to the container. More preferably the coupling arrangement is a screw fitting wherein the dispensing head is screw-fitted to the container. In these embodiments the medical lubricant applicator is reusable.

Preferably the dispensing head includes a cap configured to removably fit to the nozzle for closure of the discharge opening. More preferably the cap is coupled to the dispensing head via a flexible lanyard at opposing ends connected to the cap and the coupling arrangement, respectively.

According to a second aspect of the invention there is provided a dispensing head of a medical lubricant applicator, said dispensing head comprising:
an ejector having one or more discharge openings from which a medical lubricant is ejected;
a guide element arranged relative to the ejector to provide guiding contact with an exposed surface of a medical instrument to which ejected medical lubricant is to be applied whereby in operation said lubricant is with the assistance of the guide element directed toward the exposed surface of the medical instrument for application of said lubricant to said exposed surface via the one or more discharge openings of the ejector.

Preferably the container is at least in part formed of a flexible material adapted to discharge some of the medical lubricant on squeezing of the container. More preferably the container is constructed of a resiliently flexible material.

According to a third aspect of the invention there is provided a medical lubricant applicator comprising:
a container at least in part formed of a flexible material and being adapted to contain a medical lubricant;
a dispensing head associated with the container and designed to discharge at least some of the medical lubricant on squeezing of the container, the dispensing head including:
an ejector having one or more discharge openings from which a medical lubricant is ejected on squeezing of the container;
a guide element arranged relative to the ejector to provide guiding contact with an exposed surface of a medical instrument to which ejected medical lubricant is to be applied whereby in operation said lubricant is with the assistance of the guide element and upon hand squeezing of the container directed toward the exposed surface of the medical instrument for application of said lubricant to said exposed surface via the one or more discharge openings of the ejector.

Preferably the container is integrated with the dispensing head. More preferably the container is in the form of a sachet or cartridge. In these embodiments the medical lubricant applicator is disposable.

Preferably the ejector is integrated with the guide element which includes a contact member mounted directly to the nozzle and configured to provide contact with the exposed surface of the medical instrument for application of the medical lubricant to said exposed surface. More preferably the contact member is in profile shaped arcuate to facilitate sliding contact of the contact member with the exposed surface of the medical instrument. Even more preferably the arcuate-shaped contact member is formed of a resiliently flexible material designed for sliding contact with the exposed surface of the medical instrument whilst reducing the likelihood of damage to said exposed surface.

Alternatively the ejector is integrated with the guide element which includes a pair of arms arranged to at least in part surround the exposed surface of the medical instrument to which the medical lubricant is to be applied. In this embodiment the ejector includes one or more passageways within each of the arms, said passageways being in fluid communication with the container and the one or more discharge openings for application of the medical lubricant to the exposed surface of the medical instrument. In this case the pair of arms is resiliently flexible and thus designed to releasably surround the exposed surface of the medical instrument for sliding movement in the application of the medical lubricant.

Preferably the medical lubricant applicator is hand operated. More preferably the hand-operated applicator discharges medical lubricant by hand-squeezing of the associated container.

Preferably the medical instrument is an endoscope wherein the exposed surface is part of a longitudinal section of the sheath or other exposed surface of the shaft of the endoscope. More preferably the exposed surface is the distal end region or tip of the shaft of the endoscope.

It is to be understood that medical instrument in the context of the present invention is not limited to endoscopes but extends to colonoscopes and other medical instruments typically including elongate tubular elements intended for insertion in the human body.

BRIEF DESCRIPTION OF DRAWINGS

In order to achieve a better understanding of the nature of the present invention preferred embodiments of a medical lubricant applicator will now be described, by way of example only, with reference to the accompanying drawings in which.

DETAILED DESCRIPTION

Figure 1A:
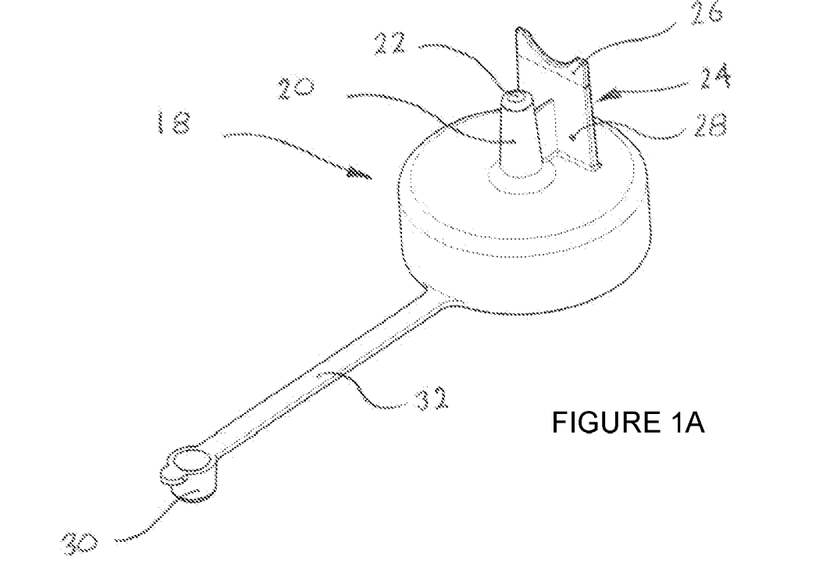
FIGS. 1A and 1B are perspective views of a dispensing head and a medical lubricant applicator in-situ according to a first embodiment of one aspect of the invention.
Figure 1B:
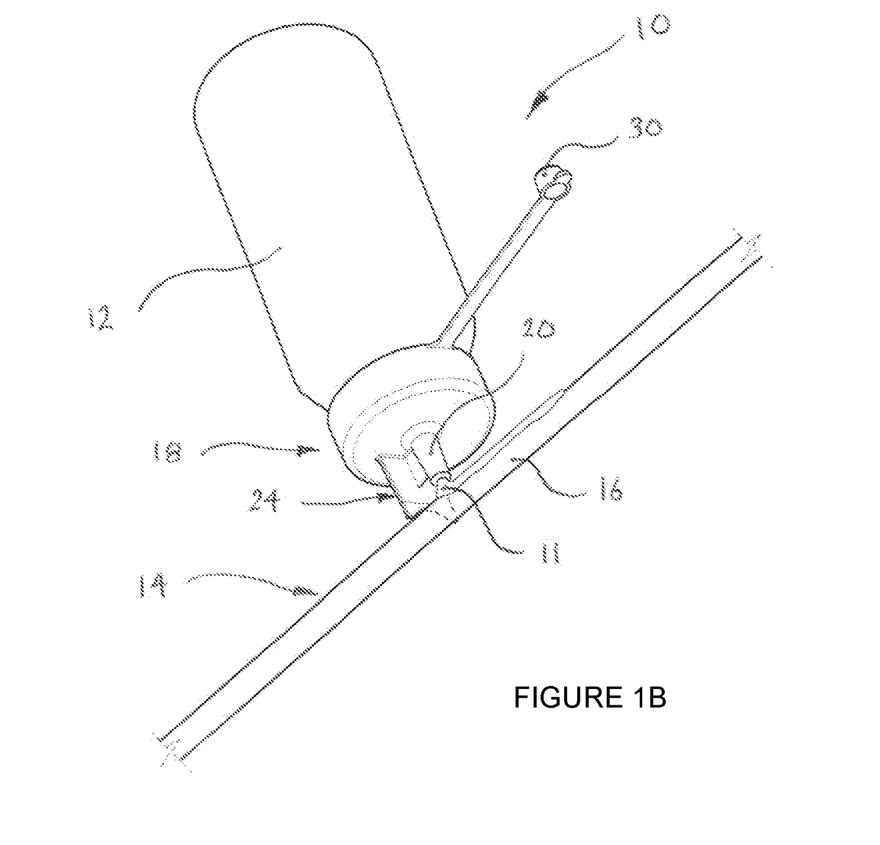

FIGS. 1A and 1B illustrate a medical lubricant applicator 10 of a first embodiment of one aspect of the invention. The medical lubricant applicator 10 is in this and other embodiments of this aspect of the invention hand-operated whereby medical lubricant 11 is discharged by hand-squeezing of an associated container 12. The medical lubricant 11 is generally in the form of a gel which is applied to a medical instrument such as an endoscope. In this application the endoscope includes a shaft 14 including an outer sheath 16 or other exposed surface to which the medical lubricant 11 is applied.

The medical lubricant applicator 10 of this embodiment comprises a dispensing head 18 adapted to fit to the container 12. The dispensing head 18 of this example includes:

1. a nozzle 20 having a discharge opening 22 from which medical lubricant 11 is dispensed;

2. a guide element 24 arranged relative to the nozzle 20 to provide guiding contact with the exposed surface or sheath 16 of the shaft 14 of the endoscope or other medical instrument.

In use, the nozzle 20 is with the assistance of the guide element 24 spaced from the shaft 14 of the medical instrument. This spacing is effective in avoiding contact between the nozzle 20 and the shaft 14 whilst the lubricant 11 is applied to the shaft 14. The spacing or air gap is intended to reduce the risk of contamination of the lubricant 11 which is expressed onto the endoscope sheath 16. The nozzle 20 is arranged relative to the guide element 24 so that the medical lubricant 11 is directed toward the exposed surface or sheath 16 of the shaft 14 reducing the likelihood of spillage.

The guide element 24 of this embodiment includes a contact member 26 mounted to a spacer member 28 arranged to space the nozzle 20 from the sheath 16 of the medical instrument. The contact member 26 is in profile shaped arcuate or in this example substantially complementary to the sheath 16 of the shaft 14. It will be understood that the arcuate-shaped contact member 26 assists with lateral location of the shaft 14 relative to the nozzle 20 to substantially align the nozzle 20 with the shaft 14 to promote application of the medical lubricant 11 to the sheath 16 of the medical instrument. In this embodiment the contact member 26 is formed of a resiliently flexible material such as Santoprene™ or other thermoplastic which facilitates sliding contact of the contact member 26 with the sheath 16 of the medical instrument whilst reducing the likelihood of damage to the sheath 16. The contact member 26 in this example may be overmoulded with Santoprene™ or other appropriate material.

The dispensing head 18 of this embodiment includes an internal screw fitting for screw fitting to a complementary screw fitting of the container 12. The medical lubricant applicator 10 is of a reusable design where on emptying of the medical lubricant from the container 12 it can be refilled for reuse typically with the same dispensing head 18. For example, the container 12 may approximately be of a 500 ml capacity which lends itself to multiple uses in lubricating the sheath 16 of the medical instrument. In its application with an endoscope it is expected that each discharge of lubricant to adequately lubricate the shaft 14 may be anywhere from around 5 ml to 20 ml.

The dispensing head 18 of this embodiment also includes a cap 30 configured to removable fit to the nozzle 20 for closure of the discharge opening 22. The cap 30 is coupled to the dispensing head 18 via a flexible lanyard 32 which at opposing ends is connected to the cap 30 and a perimeter of the dispensing head 18. It will be understood that the cap 30 when fitted to the nozzle 20 prevents spillage and/or contamination of the nozzle 20 when the lubricant applicator 10 is not in use or is in transit.

In operation, the guide element 24 of the medical lubricant applicator 10 is run along the shaft 14 of the endoscope or other medical instrument typically with the container in a substantially vertical disposition. The medical lubricant 11 may under the influence of gravity and/or in conjunction with squeezing of the container 12 discharge from the discharge opening 22 of the nozzle 20 which is spaced from the shaft 14. This sliding movement of the applicator 10 relative to the shaft 14 typically provides a continuous bead of the lubricant 11 on the sheath 16. The resiliently flexible material of the contact member 26 of this embodiment grips whilst allowing sliding contact with the sheath 16 of the shaft 14 of the medical instrument. This arrangement ensures that the nozzle 20 and discharged lubricant 11 substantially align with the shaft 14 minimising spillage. It is expected that the required lubricant coating of the sheath 16 around its exposed circumference will be effected by rubbing or smearing of the bead of lubricant 11 using a gloved hand. It is expected that, after each and every application of the lubricant gel 11 to the endoscope sheath 16, the contact member 26 or other exposed surface of the guide element 24 will be wiped clean.

Optionally the nozzle 20 may contain a device to prevent the ingress of contaminants (particularly microbial contaminants) into the container containing the lubricant gel. This ingress of contaminants may otherwise occur during or after the application of the lubricant gel 11 to the sheath 16 in the event of suck-back of the lubricant 11 into the bottle or other container 12 This device may comprise a one-way valve such as a soft flap or duckbill-style valve, or a biocidal construct such as a grid or similar included in the nozzle 20 and constructed from a biocidal metal such as silver, copper, or zinc.

Figure 2A:
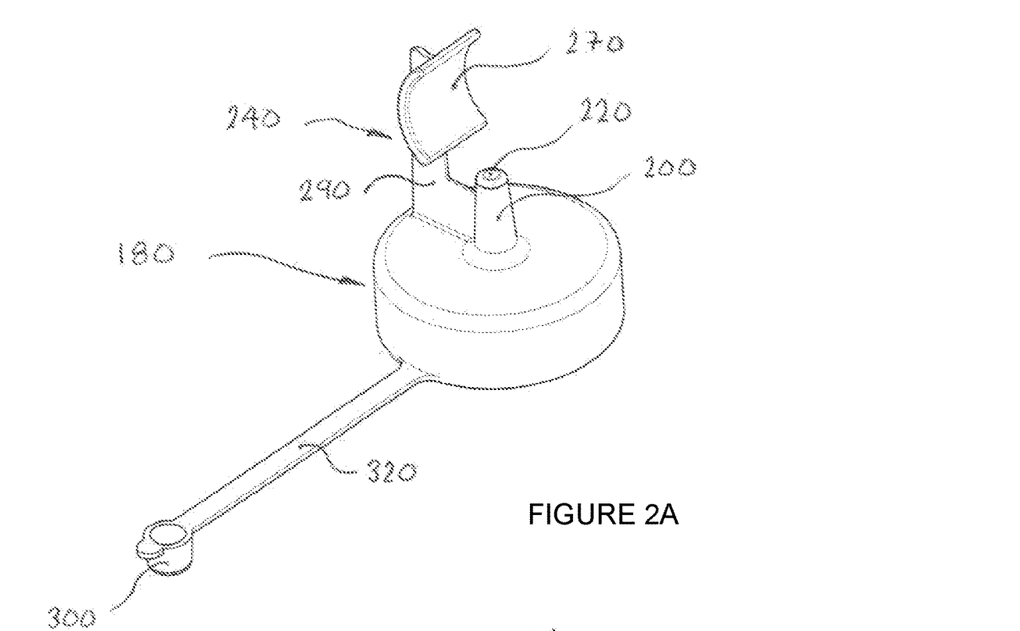
FIGS. 2A and 2B are perspective and elevational views of a dispensing head and a medical lubricant applicator in-situ according to a second embodiment of said one aspect of the invention.
Figure 2B:
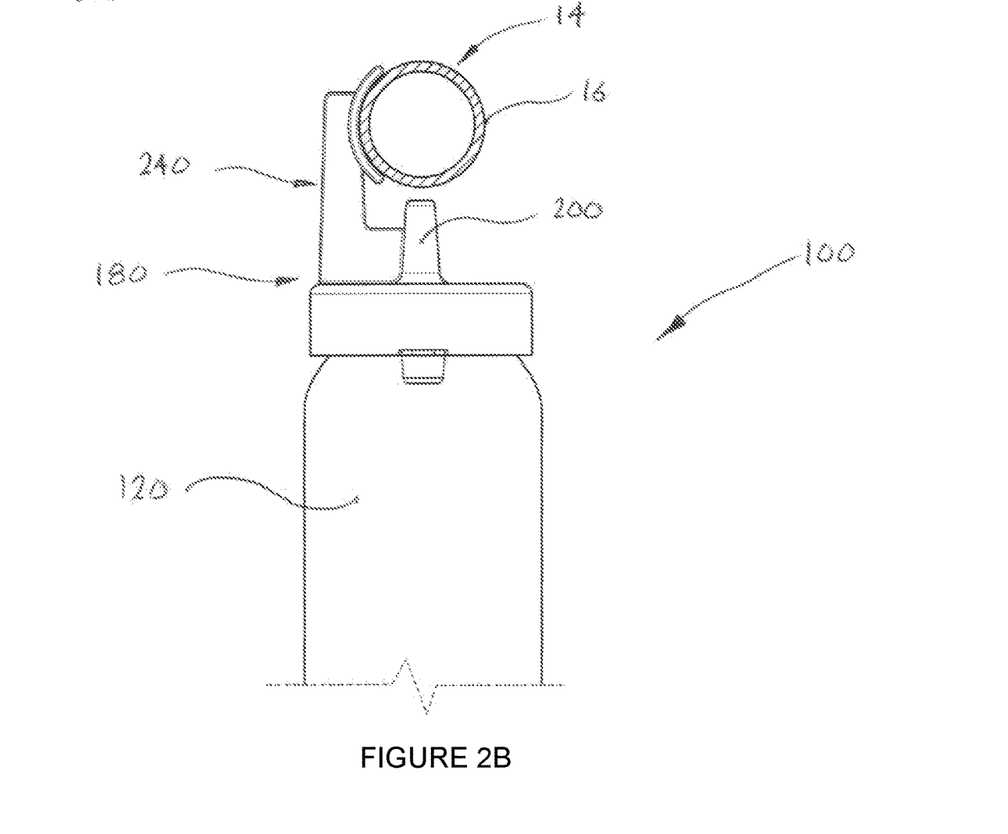

FIGS. 2A and 2B depict a second embodiment of a medical lubricant applicator 100 of the preceding aspect of the invention. For ease of reference and in order to avoid repetition, components of this embodiment generally corresponding with the preceding embodiment are designated with the same reference numeral including an additional "0". For example, the dispensing head of this second embodiment generally corresponds with the dispensing head of the first embodiment and as such has been referenced as 180.

The medical lubricant applicator 100 and dispensing head 180 of the second embodiment depart from the first embodiment insofar as:
1. the guide element 240 of the second embodiment includes a contact member 270 mounted to a spacer member 290 to laterally locate the sheath 16 or other exposed surface of the medical instrument relative to the nozzle 200;
2. the contact member 270 is in profile shaped arcuate with a complementary-shaped surface to the sheath 16 which assists with spacing of the shaft 14 from the nozzle 200 of the applicator 100.

Figure 3A:
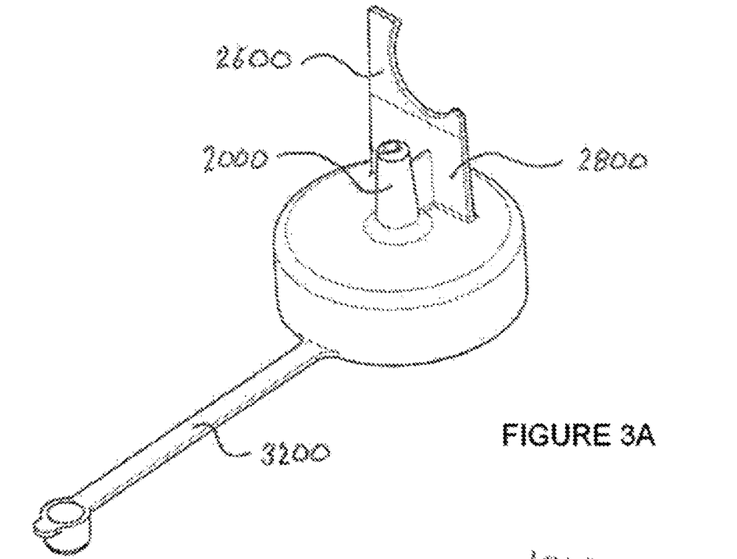
FIGS. 3A and 3B are perspective views of a dispensing head and a medical lubricant applicator in-situ according to a third embodiment of said one aspect of the invention.
Figure 3B:
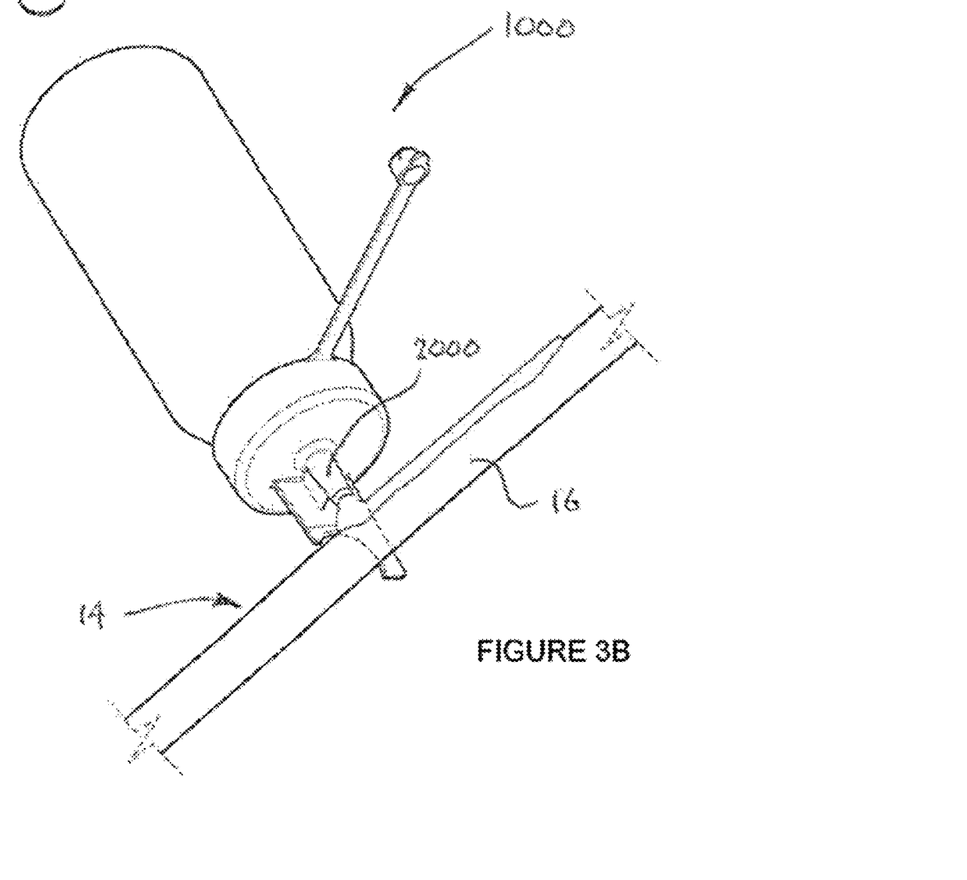

FIGS. 3A and 3B illustrate a third embodiment of a medical lubricant applicator 1000 of the preceding aspect of the invention. This third embodiment is effectively the same as the first embodiment but with improved lateral location of the shaft 14 of the medical instrument relative to the nozzle 2000. This is achieved by reconfiguring the contact member of the first embodiment whereby the contact member 2600 of this third embodiment effectively cups the sheath 16 of the shaft 14 to both separate it from the nozzle 2000 whilst laterally locating the shaft 14 relative to the nozzle 2000 to effectively direct application of the medical lubricant. In this example the contact member 2600 is in profile substantially semi-circular and complementary to the exposed sheath 16 of the shaft 14 of the medical instrument. The medical lubricant applicator 1000 of this third embodiment is otherwise of substantially the same construction as the first embodiment.

Figure 4A:
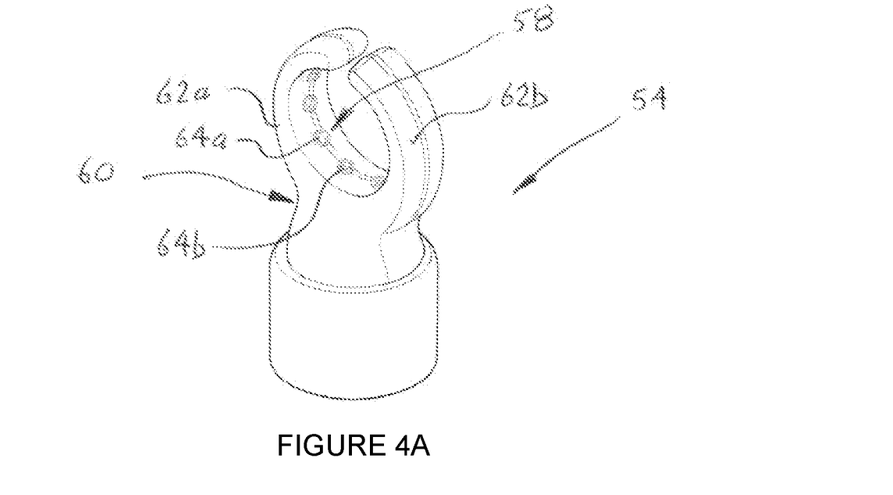
FIGS. 4A and 4B are perspective and elevational views of a dispensing head and a medical lubricant applicator in-situ according to a first embodiment of another aspect of the invention.
Figure 4B:
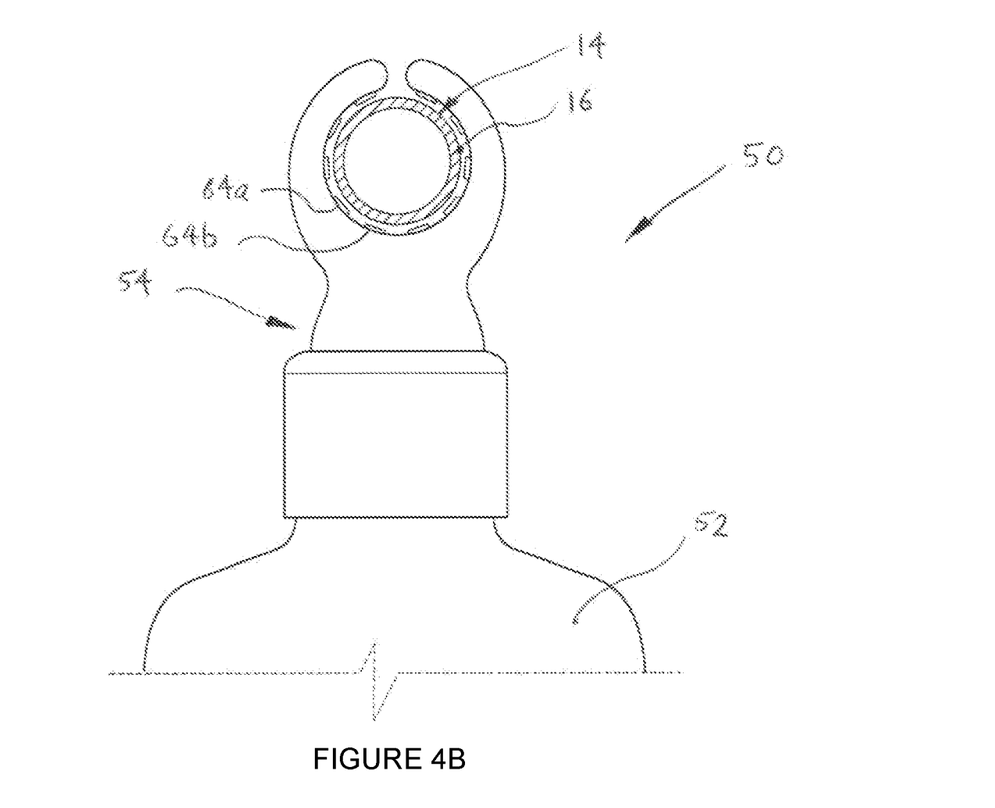

FIGS. 4A and 4B depict a first embodiment of a medical lubricant applicator 50 according to another aspect of the invention. The applicator 50 is similar to the applicators of the preceding embodiments and more generally comprises:
1. a container 52 formed of a flexible material and adapted to contain a medical lubricant;
2. a dispensing head 54 associated with the container 52 and designed to discharge at least some of the medical lubricant on squeezing of the container 52.

The dispensing head 54 includes an ejector 58 integrated with a guide element 60 in the form of a pair of arms 62a and 62b. In this embodiment the arms 62a/b are constructed of a resiliently flexible material designed to releasably locate about a shaft 14 of a medical instrument such as an endoscope. The ejector 58 of this example includes:
1. one or more discharge openings such as 64a and 64b from which the medical lubricant is ejected on squeezing of the container 52;
2. one or more passages (not shown) within each of the arms 62a/b in fluid communication with the container 52 and one or more of the discharge openings 64a/b.

In use, the medical lubricant applicator 50 locates with the pair of arms 62a/b surrounding the exposed sheath 16 of the shaft 14 of the medical instrument in preparation for its lubrication. The container 52 is then hand-squeezed to eject the medical lubricant from the discharge openings such as 64a/b whilst the dispensing head 54 is run along the shaft 14 of the medical instrument. The guide element 60 provides guiding contact of the dispensing 54 with the shaft 14 of the medical instrument or endoscope during application of the medical lubricant to the sheath 16 or other exposed surface.

The container 52 of this first embodiment may either be detachably fitted to or integrated with the dispensing head 54. In the event the container 52 is integrated with the dispensing head 54, the container 52 is preferably in the form of a sachet or cartridge 52 containing a relatively small and fixed volume of the medical lubricant sufficient only for a single use or application to one medical instrument, such as 10 ml of the lubricant to lubricate a distal end region or tip of the shaft of an endoscope. In this example, where the sachet or cartridge 52 is integrated with the dispensing head 54, the medical lubricant applicator 50 is disposable.

Figure 5A:
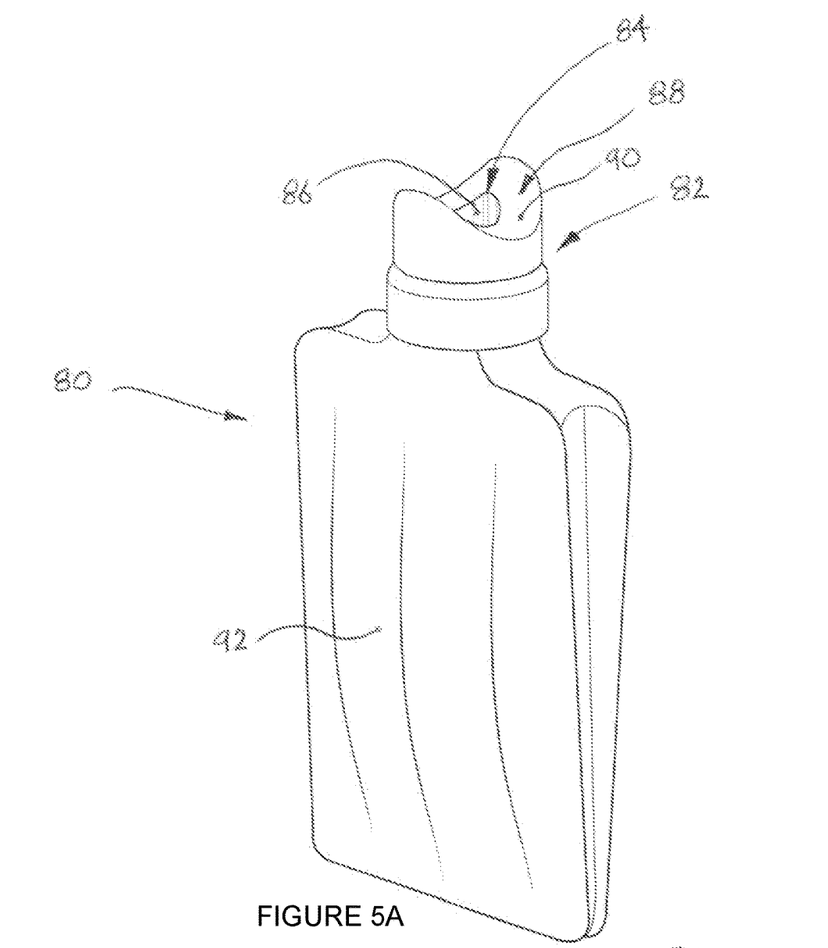
FIGS. 5A and 5B are perspective and elevational views of a medical lubricant applicator in-situ according to a second embodiment of said other aspect of the invention.
Figure 5B:
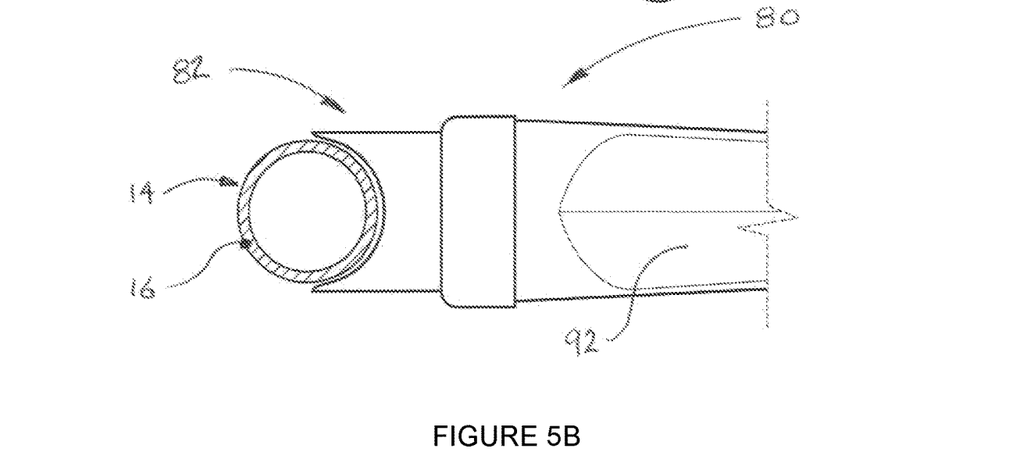

FIGS. 5A and 5B show a second embodiment of a medical lubricant applicator 80 according to this other aspect of the invention. The lubricant applicator 80 is of similar construction but of a more simplistic design to the preceding embodiment. In particular, the applicator includes a dispensing head 82 having ejector 84 in the form of a single discharge opening or orifice 86. The ejector 84 is integrated with a guide element 88 formed by a concave-shaped contact surface 90 configured to provide complementary contact with the sheath 16 of the shaft 14 of the medical instrument. The concave-shaped contact surface 90 facilitates sliding contact of the dispensing head 82 with the shaft 14 of the medical instrument. In a similar manner to earlier embodiments, the contact surface 90 is formed of a resiliently flexible material designed to reduce the likelihood of damage to the sheath 16 to which the medical lubricant is directly applied.

In this second embodiment the dispensing head 82 is integrated with an appropriate container 92 having a relatively small and single-dose capacity of the medical lubricant. In this case the container 92 is in the form of a sachet or cartridge 92 and in a similar fashion to the preceding embodiment the medical lubricant applicator is disposable.

Now that preferred embodiments of the medical lubricant applicator have been described it will be apparent to those skilled in the art that they have at least the following advantages:
1. the lubricant applicator and dispensing head of the first aspect of the invention prevent contact between the nozzle and the medical instrument thus reducing the risk of cross-contamination and infection;

2. the dispensing head of in particular the first aspect of the invention lends itself to detachable fitting to a conventional container or squeezable bottle and thus is reusable;
3. the medical lubricant applicator of the second aspect of the invention in a single-use and disposable design is effective in infection prevention;
4. both aspects of the medical lubricant applicator and dispensing head are effective in guiding the shaft or other medical instrument relative to the nozzle from which the medical lubricant is dispensed thereby minimising spillage of said lubricant.

Those skilled in the art will appreciate that the invention as described herein is susceptible to variations and modifications other than those specifically described. For example, the guide element of the dispensing head may vary in its shape and/or configuration provided the guide element assists with directed application of the medical lubricant to the medical instrument via the nozzle or ejector. The nozzle or ejector may also vary from that described and illustrated provided it permits the delivery of medical lubricant from the container to the exposed surface of the medical instrument. All such variations and modifications are to be considered within the scope of the present invention the nature of which is to be determined from the foregoing description.

The invention claimed is:

1. A medical lubricant applicator when used for applying medical lubricant to an exposed surface of medical instrument, said applicator comprising:
   a container which contains a medical lubricant, said container fitted with a dispensing head, the dispensing head including:
   i) a nozzle having a discharge opening from which medical lubricant from the container is dispensed from the container through the nozzle and applied onto said exposed surface;
   ii) a guide element arranged relative to the nozzle to provide guiding contact with said exposed surface of said medical instrument, to which the dispensed medical lubricant is applied, whereby, in operation, the nozzle is with the assistance of the guide element spaced from the exposed surface of the medical instrument to avoid contact with said exposed surface whilst the medical lubricant is directed toward the exposed surface for application of said lubricant to said exposed surface via the discharge opening of the nozzle;
   wherein the dispensing head includes a cap configured to removably fit to the nozzle for closure of the discharge opening;
   wherein the guide element includes a contact member mounted to a spacer member arranged to space the nozzle from the exposed surface of the medical instrument; and
   wherein the contact member is in profile shaped arcuate to assist with location of the medical instrument relative to the nozzle to promote application of the medical lubricant to the exposed surface of the medical instrument.

2. The medical lubricant applicator as claimed in claim 1 wherein the contact member is at least in part formed of a resiliently flexible material adapted to facilitate sliding contact of the contact member with the exposed surface of the medical instrument whilst reducing of damage to said exposed surface.

3. The medical lubricant applicator as claimed in claim 1 wherein the dispensing head also includes a coupling arrangement for detachable fitting to the container.

4. The medical lubricant applicator as claimed in claim 3 wherein the coupling arrangement is a screw fitting wherein the dispensing head is screw-fitted to the container.

5. The medical lubricant applicator as claimed in claim 3 wherein the medical lubricant applicator is reusable.

6. The medical lubricant applicator as claimed in claim 1 wherein the cap is coupled to the dispensing head via a flexible lanyard at opposing ends connected to the cap and the coupling arrangement, respectively.

7. The medical lubricant applicator as claimed in claim 6 wherein the container is at least in part formed of a flexible material adapted to discharge some of the medical lubricant on squeezing of the container.

8. The medical lubricant applicator as claimed in claim 7 wherein the container is constructed of a resiliently flexible material.

9. The medical lubricant applicator as claimed in claim 1 a wherein the nozzle is designed to discharge at least some of the medical lubricant on squeezing of the container.

10. The medical lubricant applicator as claimed in claim 1 wherein the container is integrated with the dispensing head.

11. The medical lubricant applicator as claimed in claim 1 wherein the container is in the form of a sachet or cartridge.

12. The medical lubricant applicator as claimed in claim 1 wherein the medical instrument is an endoscope wherein the exposed surface is part of a longitudinal section of a sheath or other exposed surface of a shaft of the endoscope.

* * * * *